United States Patent
Teng et al.

(10) Patent No.: US 10,538,547 B2
(45) Date of Patent: Jan. 21, 2020

(54) MANGIFERIN-6-O-CALCIUM SALT AND PREPARATION PROCESS THEREOF

(71) Applicant: CHANGZHOU DEZE MEDICAL SCIENCE CO., LTD, Changzhou (CN)

(72) Inventors: Houlei Teng, Changzhou (CN); Wei Wu, Changzhou (CN)

(73) Assignee: CHANGZHOU DEZE MEDICAL SCIENCE CO., LTD, Changzhou (CN)

( * ) Notice: Subject to any disclaimer, the term of this patent is extended or adjusted under 35 U.S.C. 154(b) by 0 days.

(21) Appl. No.: 16/231,960

(22) Filed: Dec. 25, 2018

(65) Prior Publication Data

US 2019/0127410 A1 May 2, 2019

Related U.S. Application Data

(63) Continuation of application No. PCT/CN2017/090489, filed on Jun. 28, 2017.

(30) Foreign Application Priority Data

Jul. 4, 2016 (CN) ............................ 2016 1 0510307

(51) Int. Cl.
| | | |
|---|---|---|
| *C07H 1/00* | (2006.01) | |
| *C07H 1/06* | (2006.01) | |
| *C07H 7/04* | (2006.01) | |
| *C07H 7/06* | (2006.01) | |
| *C07D 455/03* | (2006.01) | |

(52) U.S. Cl.
CPC ............. *C07H 7/06* (2013.01); *C07D 455/03* (2013.01); *C07H 1/00* (2013.01); *C07H 1/06* (2013.01); *C07H 7/04* (2013.01)

(58) Field of Classification Search
None
See application file for complete search history.

(56) References Cited

U.S. PATENT DOCUMENTS 8,334,267 B2 * 12/2012 Teng ................. C07H 17/04
514/23

FOREIGN PATENT DOCUMENTS

| CN | 1919857 A | 2/2007 |
|---|---|---|
| CN | 101066275 A | 11/2007 |
| CN | 101108869 A | 1/2008 |
| CN | 101229181 A | 7/2008 |
| CN | 101461819 A | 6/2009 |
| CN | 101848922 A | 9/2010 |
| CN | 101919839 A | 12/2010 |
| CN | 101921270 A | 12/2010 |
| WO | WO2008061480 A1 | 5/2008 |

OTHER PUBLICATIONS

Gomez et al., Spectrochimica Acta Part A, vol. 64, pp. 1002-1009, 2006.*
International Search Report for PCT/CN2017/090489.

* cited by examiner

*Primary Examiner* — Traviss C McIntosh, III

(57) ABSTRACT

The present invention provides a mangiferin-6-O-calcium salt and a preparation process thereof. In addition, use of the mangiferin-6-O-calcium salt as defined in claim 1 as an intermediate in the preparation of a mangiferin-6-O-berberine salt is also provided.

15 Claims, No Drawings

MANGIFERIN-6-O-CALCIUM SALT AND PREPARATION PROCESS THEREOF

CROSS-REFERENCE TO RELATED APPLICATIONS

The present application is a continuation of international application No. PCT/CN2017/090489, filed on Jun. 28, 2017, which claims priority to Chinese Patent Application No. 201610510307.5, filed on Jul. 4, 2016, both of which are hereby incorporated by reference in its entireties.

TECHNICAL FIELD

The present invention provides a mangiferin-6-O-calcium salt and a preparation process thereof.

In addition, use of the mangiferin-6-O-calcium salt as an intermediate in the preparation of a mangiferin-6-O-berberine salt is also provided.

BACKGROUND

Mangiferin is a natural polyphenol compound, which has a molecular formula of $C_{19}H_{18}O_{11}$ and a molecular weight of 422. The mangiferin has a chemical structure as follows:

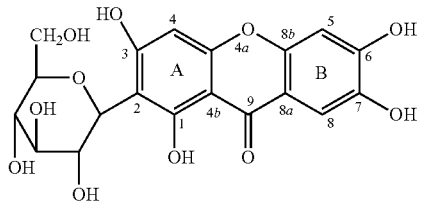

With respect to a mangiferin calcium salt, patent applications WO2009065287A1, WO2008061480A1, CN101461819, and CN101919839 have all disclosed the following contents: 1) in structure, the mangiferin calcium salt has a general formula compound (a), a mangiferin-3-O-calcium salt (b) and a mangiferin-3,7-O-calcium salt (c) whose structural formulae are as follows:

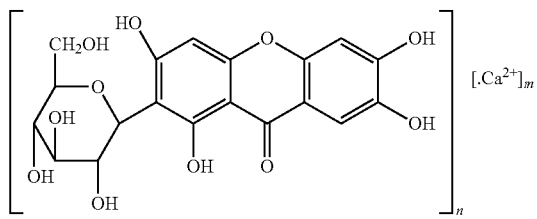

a

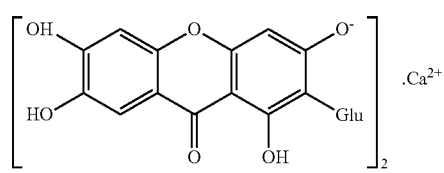

b

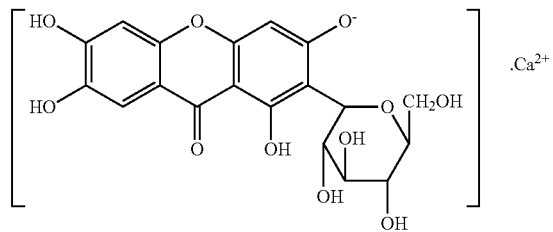

c

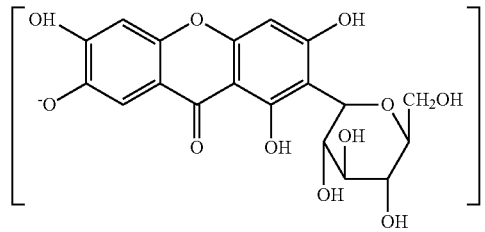

Wherein n = 1 or 2; m = 1 or 2.

2) in use, the mangiferin is medically used as an insulin sensitizer, an AMP-activated protein kinase (AMPK) activator, and an agonist of the peroxisome proliferator-activated receptor.

Patent application WO2010/145192A1 has disclosed a mangiferin berberine salt. According to the CNMR data analysis disclosed on page 5 to the second paragraph on page 7 of the description of WO2010/145192A1, the mangiferin berberine salt disclosed is a compound of a mangiferin-3-O-berberine salt and a mangiferin-7-O-berberine salt. However, a ratio of the mangiferin-3-O-berberine salt to the mangiferin-7-O-berberine salt is not given in WO2010/145192A1.

Technical Problem

According to the requirements of drug registration, the structure of new drug's raw medicine must be clear and definite. If the raw medicine is a composition, the proportion of the ingredients should be clearly defined to meet the requirement of controllable quality. Accordingly, if the mangiferin berberine salt disclosed in WO2010/145192A1 is used as the raw material, the structure thereof needs to be further clarified and defined. Analysis of the structure of the mangiferins shows that four phenolic hydroxy groups are present in the molecular structure of the mangiferin, the salt formation sites of the mangiferin have various possibilities, which increases the difficulty of yielding a mangiferin salt with a single salt formation site.

In addition, in the method for the preparation of the mangiferin berberine salt disclosed in WO2010/145192A1 (see page 4, and Examples on pages 8-10 of the description), the mangiferin is reacted with the alkaline sodium (potassium) salt to prepare a mangiferin single-sodium (potassium) salt, and the mangiferin single-sodium (potassium) salt is reacted with the berberine to generate the mangiferin berberine salt. The method has the following problems:

Since the mangiferin is originated from extracts of plants, the contents of the neo-mangiferin and the like analogues and the tanning agents and the like impurities in the raw material of the mangiferin may be greatly different due to differences of the plant category, collection time or collection site, and differences of the extraction process. In this case, in the method for the preparation of the mangiferin berberine salt disclosed in WO2010/145192A1, the feed of the raw material of the mangiferin is fabricated into a solution of the mangiferin single-sodium (potassium) salt, and the solution of the mangiferin single-sodium (potassium) salt is directly reacted with a solution of the berberine hydrochloride to prepare the mangiferin berberine salt. In this process, it is greatly probable that consistencies between batches of the mangiferin berberine salt are greatly different, and in addition, the problem of accuracy of the feed of the mangiferin is caused. If the mangiferin single-sodium (potassium) salt solid is fed to prepare the mangiferin berberine salt, ethanol, acetone or the like crystalline solvent medium needs to be used for precipitation of the mangiferin berberine salt. As such, a large amount of ethanol, acetone, ethyl acetate or the like organic solvent may be used. These organic solvents increase the cost, increase the risks of solvent residues in the mangiferin berberine salt, and additionally cause a great pressure in environmental protection in the industrial production. If a high purity mangiferin (with the content being greater than or equal to 98%) is used as the raw material, the quality of the mangiferin berberine salt is ensured. However, since the process of preparing the high purity mangiferin is complicated, the production cost of the mangiferin berberine salt is greatly increased.

SUMMARY

Technical Solution

To solve the problem that the structure needs to be clarified and defined when the mangiferin berberine salt is used as a raw material drug, and the problem that the consistency between batches in the method for the preparation of the mangiferin berberine salt disclosed in WO2010/145192A1 is poor, through deep studies, the inventors yield a mangiferin calcium salt with a single salt formation site of the mangiferin-6-O-calcium salt, and obtain a preparation process of the mangiferin-6-O-berberine salt with a single salt formation site with the mangiferin-6-O-calcium salt as an intermediate. This technical solution solves the following problems as described above:

1. In the preparation of the mangiferin-6-O-berberine salt with the mangiferin-6-O-calcium salt as the intermediate, the problem that the structure of the mangiferin berberine salt is not clarified and defined is solved.

2. In the preparation of the mangiferin-6-O-berberine salt with the mangiferin-6-O-calcium salt as the intermediate, the problem that the consistency between batches of the mangiferin berberine salt is poor is solved.

The Specific Technical Solutions are as Follows:

The present invention provides a mangiferin-6-O-calcium salt, wherein the mangiferin-6-O-calcium salt has a structure as defined in the following formula (I):

The present invention further provides a preparation process of the mangiferin-6-O-calcium salt, wherein the preparation process includes:

(1) adding an alkaline sodium salt or an alkaline potassium salt into water to yield a solution of the alkaline sodium salt or a solution of the alkaline potassium salt, the solution having a concentration of 0.1%-2% (w/v);

(2) dissolving mangiferin into dimethyl sulfoxide to yield a solution of the mangiferin;

(3) slowly adding the mangiferin solution into the solution of the alkaline sodium salt or the solution of the alkaline potassium salt, fully stirring the solution until the solution is fully reacted at a temperature of 50° C.-100° C. to yield a solution of a mangiferin sodium salt or a solution of a mangiferin potassium salt;

(4) dissolving a water-soluble calcium salt into water to yield a solution of the calcium salt;

(5) sufficiently mixing the solution of the calcium salt with the solution of the mangiferin sodium salt or the solution of the mangiferin potassium salt for full reaction, yielding a precipitate, and filtering to yield a solid; and dissolving the solid into a suitable amount of hot water, filtering and yielding a precipitate, and filtering the precipitate to obtain a solid;

(6) drying the solid to yield the mangiferin-6-O-calcium salt.

In the preparation process of the mangiferin-6-O-calcium salt according to the present invention, a ratio of the mangiferin to the dimethyl sulfoxide is 1:0.2-5 (w/v).

In the preparation process of the mangiferin-6-O-calcium salt according to the present invention, a molar ratio of the mangiferin to the alkaline sodium salt or alkaline potassium salt is 1:0.5-1.

In the preparation process of the mangiferin-6-O-calcium salt according to the present invention, a molar ratio of the mangiferin to the water-soluble calcium salt is 1:0.5-1.

In the preparation process of the mangiferin-6-O-calcium salt according to the present invention, the alkaline sodium salt or the alkaline potassium salt is one or a mixture of more than two selected from the group consisting of sodium carbonate, sodium hydrogen carbonate, potassium carbonate and potassium hydrogen carbonate; and the water-soluble calcium salt is one or a mixture of more than two selected from the group consisting of calcium chloride, calcium gluconate, calcium lactate and calcium levulinate.

The mangiferin-6-O-calcium salt obtained in the present invention may be a hydrate where each mangiferin-6-O-calcium salt molecule contains less than 9 waters.

The present invention further provides use of the mangiferin-6-O-calcium salt as an intermediate in the preparation of a mangiferin-6-O-berberine salt (formula II):

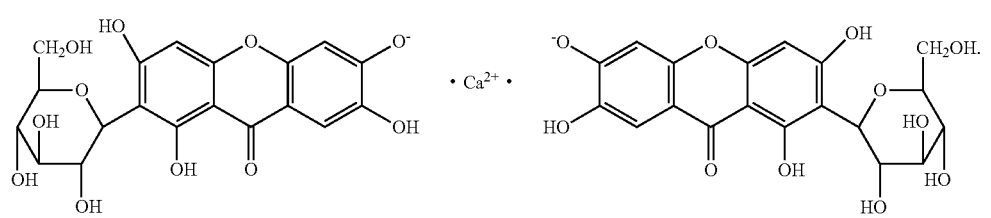

(I)

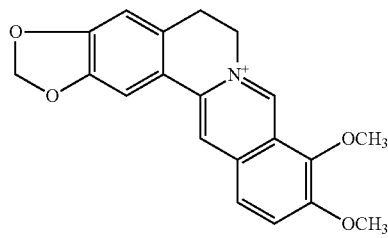
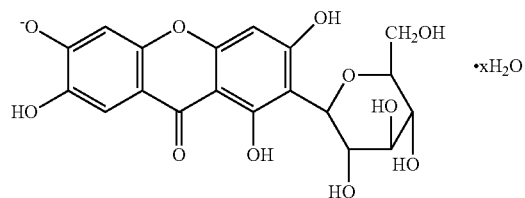

(II)

wherein 0≤x≤4.

In the use according to the present invention, the preparation of the mangiferin-6-O-berberine salt with the mangiferin-6-O-calcium salt as the intermediate includes:

(1) dissolving the mangiferin-6-O-calcium salt into 50-100° C. water to yield a solution of the mangiferin-6-O-calcium salt;

(2) dissolving berberine hydrochloride into 50-100° C. water to yield a solution of the berberine hydrochloride;

(3) sufficiently mixing the solution of the berberine hydrochloride with the solution of the mangiferin-6-O-calcium salt for full reaction to yield a precipitate, and filtering and washing the precipitate to yield a solid; and (4) drying the solid to yield the mangiferin-6-O-berberine salt.

In the preparation of the mangiferin-6-O-berberine salt with the mangiferin-6-O-calcium salt as the intermediate, the solution of the mangiferin-6-O-calcium salt has a concentration of 0.1%-3%, preferably 1%-2%; and the solution of the berberine hydrochloride has a concentration of 0.1%-4%, preferably 1%-2%.

In the preparation of the mangiferin-6-O-berberine salt with the mangiferin-6-O-calcium salt as the intermediate according to the present invention, a molar ratio of the mangiferin-6-O-calcium salt to the berberine hydrochloride is 0.5:1; and the berberine hydrochloride is substitutable by a berberine sulfate or another medically acceptable salt of berberine.

Physicochemical Properties of the mangiferin-6-O-calcium salt:

The mangiferin-6-O-calcium salt has a molecular formula $C_{38}H_{34}O_{22}Ca$, which is a light yellow-green or light yellow powder, and slightly soluble in water, soluble in hot water and slightly soluble in diluted hydrochloric acid solution. The mangiferin-6-O-calcium salt has the following structural formula:

The Spectrum Data of the mangiferin-6-O-calcium salt is as Follows:

ESI-MS (+) m/z 883 (M+H).

$^1$HNMR (400 MHz, DMSO-$d_6$) δ: 4.60 (H-1'), 6.35 (H-5), 6.23 (H-4), 7.11 (H-8). $^{13}$CNMR (400 MHz, DMSO-$d_6$) (δppm): 161.62 (C-1), 106.97 (C-2), 163.62 (C-3), 93.25 (C-4), 155.98 (C-4a), 100.53 (C-4b), 100.89 (C-5), 164.74 (C-6), 147.10 (C-7), 103.27 (C-8), 106.22 (C-8a), 153.52 (C-8b), 177.79 (C-9), 73.51 (C-1'), 70.34 (C-2'), 79.14 (C-3'), 70.34 (C-4'), 81.37 (C-5'), 60.27 (C-6').

Addendum: The spectrum data of the mangiferin is as follows: ESI-MS m/z 421 (M$^-$), $^1$HNMR (400 MHz, DMSO-$d_6$) δ: 4.60 (H-1'), 6.01 (H-5), 6.10 (H-4), 6.96 (H-8). $^{13}$CNMR (400 MHz, DMSO-$d_6$) (δppm): 161.68 (C-1), 107.54 (C-2), 163.73 (C-3), 93.27 (C-4), 156.15 (C-4a), 101.25 (C-4b), 102.54 (C-5), 153.91 (C-6), 143.63 (C-7), 108.05 (C-8), 111.68 (C-8a), 150.7 (C-8b), 179.02 (C-9), 73.04 (C-1'), 70.24 (C-2'), 78.90 (C-3'), 70.56 (C-4'), 81.44 (C-5'), 61.41 (C-6').

By using the plasma emission spectral analysis, it is tested that the content of the calcium element in the mangiferin calcium salt is $4.5 \times 10^4$ mg/kg.

Structural Analysis:

A carbon NMR data comparison between the mangiferin calcium salt and the mangiferin reveals that: the chemical shifts of the B-ring carbon atoms in the mangiferin change greatly, wherein the chemical shifts of the carbon atoms C-6 and C-7 remarkably change due to the deshielding effect, the chemical shift of C-6 most remarkably changes; and the chemical shifts of the carbon atoms C-5, C-8, C-8a and C-8b change to different degrees due to the shielding effect, wherein the chemical shifts of C-8 and C-8a which lie in the meta position and para position of C-6 change more remarkably.

A hydrogen NMR data comparison between the mangiferin calcium salt and the mangiferin reveals that: the chemical shifts of hydrogen atoms H-8, H-5 and H-4 change to different degrees due to the shielding effect, wherein the chemical shift of the hydrogen atom H-5 most remarkably change.

Electrospray ionization mass spectrometry (+) ESI: 883 (M+H).

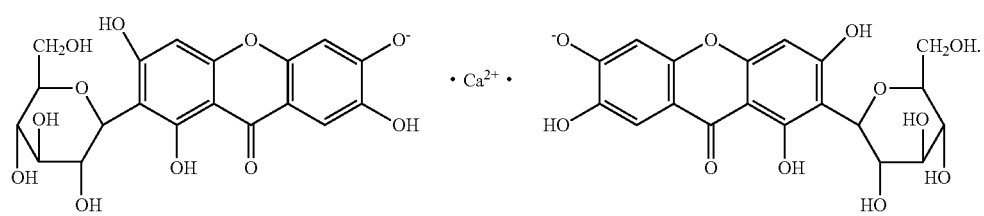

(I)

The mass spectral data reveals that the molecular weight of the mangiferin calcium slat is 882, which indicates that two molecules of mangiferin ions are bonded to one molecule of calcium.

By using the plasma emission spectral analysis, it is tested that the content of the calcium element in the mangiferin calcium salt is $4.5\times10^4$ mg/kg (the theoretical value is $4.5\times10^4$ mg/kg).

According to the above spectroscopy data, the mangiferin calcium salt has the chemical structure as follows: two molecules of mangiferin-6-O— are bonded to $Ca^{2+}$, thereby forming the mangiferin-6-O-calcium salt.

Beneficial Effects (1) The mangiferin-6-O-calcium which has a high purity, stability and storage convenience may be prepared by using the crude mangiferin raw material (for example, the extracts having the content of the mangiferin of 80% or 90%) as an intermediate raw material; the mangiferin-6-O-calcium salt is prepared by using the crude mangiferin raw material. In this way, the production cost may be greatly lowered (the price of the crude mangiferin raw material having the content of the mangiferin of 80% to 90% is ⅓, or even less, that of the high purity mangiferin with the content being greater than or equal to 98%), and the pressure in environmental protection may be reduced.

(2) The preparation of the mangiferin-6-O-berberine salt with the mangiferin-6-O-calcium salt as the intermediate may improve the purity of the mangiferin-6-O-berberine salt, simplify the process for purifying the mangiferin-6-O-berberine salt (as disclosed in WO2010/145192A1, the purity of the mangiferin berberine salt is less than 99%, and if the mangiferin berberine salt with a purity of over 99% is desired, the purification is needed), and lower the cost of preparing the mangiferin-6-O-berberine salt.

Experimental Example 1: Study Result of Physiochemical Properties of the mangiferin-6-O-berberine salt The mangiferin-6-O-berberine salt has a molecular formula of $C_{20}H_{18}NO_4 \cdot C_{19}H_{17}O_{11} \cdot xH_2O$, which is an orange yellow powder, and has a melting point of 177° C.-179° C. The mangiferin-6-O-berberine salt has the following structural formula:

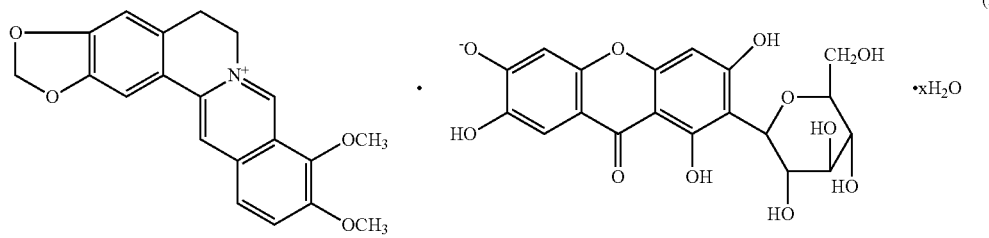

(II)

wherein $0 \leq x \leq 4$.

The spectrum data of the mangiferin-6-O-berberine salt is as follows: ESI-MS (−) m/z 756 (M⁻), 421; ESI-MS (+) m/z 336, 423; the data of the mangiferin group is as follows: $^1$HNMR (400 MHz, DMSO-$d_6$) δ: 4.56 (H-1'), 6.01 (H-5), 6.15 (H-4), 6.88 (H-8). $^{13}$CNMR (400 MHz, DMSO-$d_6$) δ: 161.51 (C-1), 106.58 (C-2), 163.06 (C-3), 92.77 (C-4), 155.55 (C-4a), 103.74 (C-4b), 98.64 (C-5), 166.93 (C-6), 147.03 (C-7), 100.47 (C-8), 100.53 (C-8a), 154.37 (C-8b), 176.73 (C-9), 73.51 (C-1'), 70.34 (C-2'), 79.14 (C-3'), 70.34 (C-4'), 81.37 (C-5'), 61.27 (C-6'). Data of the berberine group is as follows: $^1$HNMR (400 MHz, DMSO-$d_6$) δ: 3.2 (H-5), 4.03 (—OCH3), 4.07 (—OCH3), 4.89 (H-6), 6.13 (—O—CH2—O—), 7.01 (H-4), 7.69 (H-1), 7.86 (H-12), 8.07 (H-11), 8.78 (H-13), 9.78 (H-8). $^{13}$CNMR (400 MHz, DMSO-$d_6$) δ: 105.33(C-1), 120.29 (C-1a), 147.56 (C-2), 149.71 (C-3), 108.22 (C-4), 130.45 (C-4a), 26.28 (C-5), 55.07 (C-6), 145.06 (C-8), 121.24 (C-8a), 143.51 (C-9), 150.15 (C-10), 126.55 (C-11), 123.33 (C-12), 132.87 (C-12a), 120.08 (C-13), 137.3 (C-13a), 56.93 (C10(—OCH$_3$)), 61.74 (C9(—OCH$_3$)), 101.96 (—O—CH$_2$—O—).

Addendum: The spectrum data of the mangiferin is as follows: ESI-MS m/z 421 (M−); $^1$HNMR (400 MHz, DMSO-$d_6$) δ: 4.60 (H-1'), 6.37 (H-5), 6.86 (H-4), 7.39 (H-8). $^{3}$CNMR (400 MHz, DMSO-do) δ: 161.68 (C-1), 107.54 (C-2), 163.73 (C-3), 93.27 (C-4), 156.15 (C-4a), 101.25 (C-4b), 102.54 (C-5), 153.91 (C-6), 143.63 (C-7), 108.05 (C-8), 111.68 (C-8a), 150.7 (C-8b), 179.02 (C-9), 73.04 (C-1'), 70.24 (C-2'), 78.9 (C-3'), 70.56 (C-4'), 81.44 (C-5'), 61.41 (C-6').

The spectrum data of the berberine is as follows: ESI-MS m/z 336 (M); $^1$HNMR (400 MHz, DMSO-$d_6$) δ: 3.26 (H-5), 4.11 (—OCH3), 4.21 (—OCH3), 4.92 (H-6), 6.11 (—O—CH2-O—), 6.96 (H-4), 7.66 (H-1), 8.0 (H-12), 8.11 (H-11), 8.7 (H-13), 9.76 (H-8). $^{13}$CNMR (400 MHz, DMSO-$d_6$) δ: 106.54 (C-1), 121.49 (C-1a), 149.92 (C-2), 152.17 (C-3), 109.40 (C-4), 131.90 (C-4a), 28.24 (C-5), 57.20 (C-6), 145.73 (C-8), 123.33 (C-8a), 146.42 (C-9), 152.02 (C-10), 128.04 (C-11), 124.55 (C-12), 135.13 (C-12a), 121.86 (C-13), 139.65 (C-13a), 57.61 (C10(—OCH$_3$)), 62.56 (C9 (—OCH$_3$)), 103.68 (—O—CH$_2$—O—).

Structural Analysis:

Compared with a berberine prototype compound, as disclosed in the carbon spectrum data, the chemical shifts of the carbon atoms in the berberine group in mangiferin-6-O-berberine salt change remarkably due to the shielding effect.

Compared with a mangiferin prototype compound, as disclosed in the carbon spectrum data, the chemical shifts of the carbon atoms $C_6$, $C_7$ and $C_{8b}$ in the mangiferin group change remarkably due to the deshielding effect, wherein the chemical shift of $C_6$ changes most remarkably among them; and the chemical shifts of the carbon atoms $C_5$, $C_8$ and $C_{8a}$ also change to different degrees due to the shielding effect, wherein the chemical shifts of $C_8$ and $C_{8a}$ which lie in the meta position and para position of $C_6$ change more remarkably.

According to the above spectrum data analysis, it may be known that mangiferin-6-O— is combined with berberine —N⁺, and the mangiferin-6-O-berberine salt is yielded.

Elemental analysis data of the mangiferin-6-O-berberine salt and the hydrates thereof:

| | Mass fraction, % | | | | | |
|---|---|---|---|---|---|---|
| | C | | H | | N | |
| Samples | Theoretical value | Measured value | Theoretical value | Measured value | Theoretical value | Measured value |
| Mangiferin-6-O-berberine salt | 61.82 | 61.57 | 4.62 | 4.70 | 1.85 | 1.84 |
| Dihydrate of Mangiferin-6-O-berberine salt | 59.02 | 58.73 | 4.92 | 4.93 | 1.77 | 1.72 |
| Tetrahydrate of Mangiferin-6-O-berberine salt | 56.45 | 56.24 | 5.19 | 5.20 | 1.69 | 1.67 |

Experimental Example 2: Quality Inspection Between Batches of the mangiferin-6-O-berberine salt By using two preparation processes, the mangiferin-6-O-berberine salts were respectively prepared with the mangiferin raw materials having different specifications, with the contents of 80%, 90& and 98%, and the purities of the obtained mangiferin-6-O-berberine salts were compared.

1. The mangiferin was prepared into a mangiferin-6-O-calcium salt, and then a solution of the mangiferin-6-O-calcium salt was reacted with a solution of the berberine hydrochloride to prepare the mangiferin-6-O-berberine salt (which is referred to as the calcium salt approach, that is, the preparation process of the mangiferin-6-O-berberine salt in the summary of the present invention).

2. The mangiferin was prepared into a solution of a sodium salt, and directly reacted with the solution of the berberine hydrochloride to prepare the mangiferin-6-O-berberine salt (which is referred to as the sodium salt approach).

Preparation of the mangiferin-6-O-berberine salt based on a "sodium salt approach" includes the following steps:

(1) adding an alkaline sodium salt or an alkaline potassium salt into water to yield a solution of the alkaline sodium salt or a solution of the alkaline potassium salt, the solution having a concentration of 0.1%-2% (w/v);

(2) dissolving mangiferin into dimethyl sulfoxide to yield a solution of the mangiferin;

(3) slowly adding the mangiferin solution into the solution of the alkaline sodium salt or the solution of the alkaline potassium salt, fully stirring the solution until the solution is fully reacted at a temperature of 50° C.–100° C. to yield a solution of a mangiferin-6-O-sodium salt or a solution of a mangiferin-6-O-potassium salt;

(4) dissolving berberine hydrochloride into 50° C.–100° C. water to yield a solution of the berberine hydrochloride;

(5) sufficiently mixing the solution of the berberine hydrochloride with the solution of the mangiferin-6-O-sodium salt or the solution of the mangiferin-6-O-potassium salt for full reaction to yield a precipitate, and filtering and washing the precipitate to yield a solid; and (6) drying the solid to yield the mangiferin-6-O-berberine salt.

Sample Testing Method:

A chromatographic column was filled with octadecylsilanized silica gel; the mobile phase was methanol-water (0.05 mol/l of potassium hydrogen phosphate)=40:60, the wavelength was 260 nm, and the flow rate was 1 ml/min.

A suitable amount of the mangiferin-6-O-berberine salt sample was weighed and placed into a 25 ml flask, the mobile phase was added for dissolving the sample and yielding a solution thereof, 2 ml of the mother liquid was injected into a 10 ml flask, the mobile phase was added for dilution to a scale, the solution was shaken to yield a solution.

The above two solutions for comparison and testing, 10 μl for each, were respectively suctioned to the liquid chromatographer for testing, and the purities thereof were tested by using the area normalization method. The results were as listed as follows:

| | | Purity of mangiferin-6-O-berberine salt | |
|---|---|---|---|
| Batch | Specification of mangiferin | Calcium salt approach | Sodium salt approach |
| 150312 | 80% | 99.5% | 75.3% |
| 150317 | 90% | 99.6% | 88.1% |
| 150321 | 98% | 99.6% | 98.5% |

In conclusion:

With respect to the mangiferin-6-O-berberine salt prepared based on the "sodium salt approach", consistency between batches is poor; whereas with respect to the mangiferin-6-O-berberine salt prepared based on the "calcium salt approach", consistency between batches is good.

With respect to the mangiferin-6-O-berberine salt prepared from the mangiferin materials with different specifications based on the "sodium salt approach", consistency between batches is poor.

With respect to the mangiferin-6-O-berberine salt prepared from the mangiferin materials with different specifications based on the "calcium salt approach", consistency between batches is good.

Experimental Example 3: Stability of the mangiferin-6-O-calcium salt

1) Room Temperature Long-Term Stability Test

Test method: A sample of the mangiferin-6-O-calcium salt raw material was sealingly packaged with an aluminum plastic composition bag, placed at 25° C.±2° C. and 60% RH±5% RH conditions, pieces of the sample were taken at the time of 0, 3, 6, 9 and 12 months and the morphology and content thereof were tested. The test results were as listed as follows:

| | Inspection result of room temperature long-term stability test (batch 140618) | | | | |
|---|---|---|---|---|---|
| | Time of standing | | | | |
| Item | 0 month | 3 months | 6 months | 9 months | 12 months |
| Morphology | Light yellow-green powder | Light yellow-green powder | Light yellow-green powder | Light yellow-green powder | Light yellow-green powder |
| Content | 84.5% | 84.5% | 84.3% | 84.6% | 84.2% |

Conclusion: The mangiferin-6-O-calcium salt has stable properties after being placed under the room temperature condition for 12 months.

2) Acceleration Test

Test method: A sample of the mangiferin-6-O-calcium salt raw material was sealingly packaged with an aluminum plastic composition bag, placed at 40° C.±2° C. and 75% RH±5% RH conditions, pieces of the sample were taken at the time of 0, 3 and 6 months and the morphology and content thereof were tested. The test results were as listed as follows:

| Inspection result of acceleration test (batch 140618) | | | |
|---|---|---|---|
| | Time of standing | | |
| Item | 0 month | 3 months | 6 months |
| Morphology | Light yellow-green powder | Light yellow-green powder | Light yellow-green powder |
| Content | 84.5% | 84.5% | 84.2% |

Conclusion: The mangiferin-6-O-calcium salt has stable properties after being placed under the acceleration test condition for 6 months.

BRIEF DESCRIPTION OF THE DRAWINGS

None.

DETAILED DESCRIPTION

Preferred Example

Example 1: Preparation of the mangiferin-6-O-calcium salt 1680 ml of water was added into a reactor, and 0.1 mol of sodium hydrogen carbonate was added into the water to formulate a solution of the sodium hydrogen carbonate having a concentration of 0.5% (w/v); 0.1 mol of mangiferin (with the content of 95%) was added into 85 ml of DMSO (a ratio of the mangiferin to the DMSO was 1:2 (w/v)) and then heated and dissolved to formulate a solution of the mangiferin; the solution of the mangiferin was slowly added into the solution of the sodium hydrogen carbonate and sufficiently stirred, a temperature thereof was maintained at 85° C. for full reaction, and a resulted product was filtered for future use; 0.05 mol of anhydrous calcium chloride was weighed and added into 500 ml of water and dissolved therein, a solution of the calcium chloride was added into a reacted solution of the mangiferin and sufficiently stirred, the temperature was lowered to yield a precipitate, the temperature was then lowered to the room temperature, the precipitate was stood still overnight, and the reacted liquid was filtered; a resulted precipitate was added into hot water and dissolved therein, and then filtered, the temperature of a filtrate was lowered to yield a precipitate, the precipitate was then placed still at the room temperature overnight and filtered, the precipitate was vacuum dried at 60° C. and ground to yield the mangiferin-6-O-calcium salt in the form of a light yellow powder. A yield rate was 74.5%, and a sample purity was 99.5% through a high performance liquid chromatography (HPLC) measurement.

EXAMPLES

The mangiferin according to the present invention are purchased from market (Xi'an Realin Biotechnology Co., Ltd, and manufacturers having the corresponding extraction machines are all capable of producing the mangiferin). The berberine hydrochloride, the berberine sulfate and the like are all purchased from market (Xi'an XiaoCao Botanical Development Co., Ltd.). The sodium carbonate, sodium hydrogen carbonate, potassium carbonate, potassium hydrogen carbonate, dimethyl sulfoxide (DMSO), anhydrous calcium chloride, calcium chloride, calcium gluconate, calcium lactate, calcium levulinate and the like reagents are all purchased from market.

Example 2: Preparation of the mangiferin-6-O-calcium salt 2000 ml of water was added into a reactor, and 0.1 mol of sodium hydrogen carbonate was added into the water to formulate a solution of the sodium hydrogen carbonate having a concentration of 0.4% (w/v); 0.1 mol of mangiferin (with the content of 90%) was added into 127 ml of DMSO (a ratio of the mangiferin to the DMSO was 1:3 (w/v)) and then heated and dissolved to formulate a solution of the mangiferin; the solution of the mangiferin was slowly added into the solution of the sodium hydrogen carbonate and sufficiently stirred, a temperature thereof was maintained at 80° C. for full reaction, and a resulted product was filtered for future use; 0.05 mol of anhydrous calcium chloride and 0.025 mol of calcium gluconate were weighed and added into 1000 ml of water and dissolved therein, a mixed solution of the calcium chloride and the calcium gluconate was added into a reacted solution of the mangiferin and sufficiently stirred, the temperature was lowered to yield a precipitate, the temperature was then lowered to the room temperature, the precipitate was stood still overnight, and the reacted liquid was filtered; a resulted precipitate was added into hot water and dissolved therein, and then filtered, the temperature of a filtrate was lowered to yield a precipitate, the precipitate was then placed still at the room temperature overnight and filtered, the precipitate was vacuum dried at 50° C. and ground to yield the mangiferin-6-O-calcium salt in the form of a light yellow powder. A yield rate was 70.5%, and a sample purity was 99.6% through a high performance liquid chromatography (HPLC) measurement.

Example 3: Preparation of the mangiferin-6-O-calcium salt 3500 ml of water was added into a reactor, and 0.05 mol of sodium carbonate was added into the water to formulate a solution of the sodium carbonate having a concentration of 0.3% (w/v); 0.1 mol of mangiferin (with the content of 80%) was added into 169 ml of DMSO (a ratio of the mangiferin to the DMSO was 1:4 (w/v)) and dissolved to formulate a solution of the mangiferin; the solution of the mangiferin was slowly added into the solution of the sodium carbonate and sufficiently stirred, a temperature thereof was maintained at 100° C. for full reaction, and a resulted product was filtered for future use; 0.06 mol of calcium gluconate was weighed and added into 100 ml of hot water and dissolved therein, a solution of the calcium gluconate was added into a reacted solution of the mangiferin and sufficiently stirred, the temperature was lowered to yield a precipitate, the temperature was then lowered to the room temperature, the precipitate was stood still overnight, and the reacted liquid was filtered; a resulted precipitate was added into hot water and dissolved therein, and then filtered, the temperature of a filtrate was lowered to yield a precipitate, the precipitate was then stood still at the room temperature overnight and filtered, the precipitate was vacuum dried at 55° C. and ground to yield the mangiferin-6-O-calcium salt in the form of a light yellow powder. A yield rate was 70.1%, and a sample purity was 99.3% through a high performance liquid chromatography (HPLC) measurement.

Example 4: Preparation of the mangiferin-6-O-calcium salt 13800 ml of water was added into a reactor, and 0.06 mol of potassium carbonate was added into the water to formulate a solution of the potassium carbonate having a concentration of 0.1% (w/v); 0.1 mol of mangiferin (with the content of 98%) was added into 210 ml of DMSO (a ratio of the mangiferin to the DMSO was 1:5 (w/v)) and dissolved to formulate a solution of the mangiferin; the solution of the mangiferin was slowly added into the solution of the potassium carbonate and sufficiently stirred, the temperature thereof was maintained at 50° C. for full reaction, and a resulted product was filtered for future use; 0.07 mol of calcium lactate was weighed and added into 100 ml of hot water and dissolved therein, a solution of the calcium lactate was added into a reacted solution of the mangiferin and sufficiently stirred, the temperature was lowered to yield a precipitate, the temperature was then lowered to the room temperature, the precipitate was stood still overnight, and the reacted liquid was filtered; a resulted precipitate was added into hot water and dissolved therein, and then filtered, the temperature of a filtrate was lowered to yield a precipitate, the precipitate was then stood still at the room temperature overnight and filtered, the precipitate was vacuum dried at 55° C. and ground to yield the mangiferin-6-O-calcium salt in the form of a light yellow powder. A yield rate was 65.7%, and a sample purity was 99.4% through a high performance liquid chromatography (HPLC) measurement.

Example 5: Preparation of the mangiferin-6-O-calcium salt 670 ml of water was added into a reactor, and 0.1 mol of potassium hydrogen carbonate was added into the water to formulate a solution of the potassium hydrogen carbonate having a concentration of 1.5% (w/v); 0.1 mol of mangiferin (with the content of 90%) was added into 21 ml of DMSO (a ratio of the mangiferin to the DMSO was 1:0.5 (w/v)) and then heated and dissolved to formulate a solution of the mangiferin; the solution of the mangiferin was slowly added into the solution of the potassium hydrogen carbonate and sufficiently stirred, a temperature thereof was maintained at 70° C. for full reaction, and a resulted product was filtered for future use; 0.055 mol of calcium levulinate was weighed and added into 1000 ml of water and dissolved therein, a solution of the calcium levulinate was added into a reacted solution of the mangiferin and sufficiently stirred, the temperature was lowered to yield a precipitate, the temperature was then lowered to the room temperature, the precipitate was stood still overnight, and the reacted liquid was filtered; a resulted precipitate was added into hot water and dissolved therein, and then filtered, the temperature of a filtrate was lowered to yield a precipitate, the precipitate was then placed still at the room temperature overnight and filtered, the precipitate was vacuum dried at 55° C. and ground to yield the mangiferin-6-O-calcium salt in the form of a light yellow powder. A yield rate was 72.5%, and a sample purity was 99.4% through a high performance liquid chromatography (HPLC) measurement.

Example 6: Preparation of the mangiferin-6-O-calcium salt 800 ml of water was added into a reactor, and 0.1 mol of sodium hydrogen carbonate was added into the water to formulate a solution of the sodium hydrogen carbonate having a concentration of 1% (w/v); 0.1 mol of mangiferin (with the content of 90%) was added into 8.5 ml of DMSO (a ratio of the mangiferin to the DMSO was 1:0.2 (w/v)) and then heated and dissolved to formulate a solution of the mangiferin; the solution of the mangiferin was slowly added into the solution of the sodium hydrogen carbonate and sufficiently stirred, a temperature thereof was maintained at 90° C. for full reaction, and a resulted product was filtered for future use; 0.05 mol of calcium chloride was weighed and added into 800 ml of water and dissolved therein, a solution of the calcium chloride was added into a reacted solution of the mangiferin and sufficiently stirred, the temperature was lowered to yield a precipitate, the temperature was then lowered to the room temperature, the precipitate was stood still overnight, and the reacted liquid was filtered; a resulted precipitate was added into hot water and dissolved therein, and then filtered, the temperature of a filtrate was lowered to yield a precipitate, the precipitate was then placed still at the room temperature overnight and filtered, the precipitate was vacuum dried at 55° C. and ground to yield the mangiferin-6-O-calcium salt in the form of a light yellow powder. A yield rate was 73.2%, and a sample purity was 99.6% through a high performance liquid chromatography (HPLC) measurement.

Example 7: Preparation of the mangiferin-6-O-calcium salt 380 ml of water was added into a reactor, and 0.03 mol of sodium carbonate and 0.04 mol of sodium hydrogen carbonate were added into the water to formulate a solution having a concentration of 2% (w/v); 0.1 mol of mangiferin (with the content of 80%) was added into 42 ml of DMSO (a ratio of the mangiferin to the DMSO was 1:1 (w/v)) and then heated and dissolved to formulate a solution of the mangiferin; the solution of the mangiferin was slowly added into a solution of an alkaline sodium salt and sufficiently stirred, a temperature thereof was maintained at 95° C. for full reaction, and a resulted product was filtered for future use; 0.1 mol of anhydrous calcium chloride was weighed and added into 1500 ml of water and dissolved therein, a solution of the calcium chloride was added into a reacted solution of the mangiferin and sufficiently stirred, the temperature was lowered to yield a precipitate, the temperature was then lowered to the room temperature, the precipitate was stood still overnight, and the reacted liquid was filtered; a resulted precipitate was added into hot water and dissolved therein, and then filtered, the temperature of a filtrate was lowered to yield a precipitate, the precipitate was then placed still at the room temperature overnight and filtered, the precipitate was vacuum dried at 55° C. and ground to yield the mangiferin-6-O-calcium salt in the form of a light yellow powder. A yield rate was 65.2%, and a sample purity was 99.0% through a high performance liquid chromatography (HPLC) measurement.

Preparation Example 1: Preparation of the mangiferin-6-O-berberine salt 0.05 mol of the mangiferin-6-O-calcium salt prepared in the above examples was weighed and added into a suitable amount of 100° C. water and dissolved therein to formulate a solution having a concentration of 3% (w/v), and the solution was filtered for future use; 0.1 mol of berberine sulfate was weighed and added into a suitable amount of 50° C. water and dissolved therein to formulate a solution having a concentration of 0.1% (w/v), and the solution was filtered for future use; and the solution of the berberine sulfate was slowly added into the solution of the mangiferin-6-O-calcium salt, and sufficiently stirred for full reaction, the temperature thereof is lowered to yield a precipitate, the precipitate was then filtered and washed with purified water sufficiently, a resulted solid was then vacuum dried at 50° C. and ground to yield an orange yellow solid mangiferin-6-O-berberine salt. A yield rate was 71.8%. and a sample purity was 99.6% through a high performance liquid chromatography (HPLC) measurement

Preparation Example 2: Preparation of a Tetrahydrate of the mangiferin-6-O-berberine salt 0.05 mol of the mangiferin-6-O-calcium salt prepared in the above examples was weighed and added into a suitable amount of 50° C. water and dissolved therein to formulate a solution having a concentration of 0.1% (w/v), and the solution was filtered for future use; 0.1 mol of berberine hydrochloride was weighed and added into a suitable amount of 100° C. water and dissolved therein to formulate a solution having a concentration of 4% (w/v), and the solution was filtered for future use; and the solution of the berberine hydrochloride was slowly added into the solution of the mangiferin-6-O-calcium salt, and sufficiently stirred for full reaction, the temperature thereof is lowered to yield a precipitate, the precipitate was then filtered and washed with purified water sufficiently, a resulted solid was then vacuum dried at 55° C. and ground to yield an orange yellow solid tetrahyrate mangiferin-6-O-berberine salt. A yield rate was 71.5%, and a sample purity was 99.5% through a high performance liquid chromatography (HPLC) measurement

Preparation Example 3: Preparation of a Dihydrate of the mangiferin-6-O-berberine salt 0.05 mol of the mangiferin-6-O-calcium salt prepared in the above examples was weighed and added into a suitable amount of 80° C. water and dissolved therein to formulate a solution having a concentration of 1% (w/v), and the solution was filtered for future use; 0.1 mol of berberine hydrochloride was weighed and added into a suitable amount of 70° C. water and dissolved therein to formulate a solution having a concentration of 2% (w/v), and the solution was filtered for future use; and the solution of the mangiferin-6-O-calcium salt was slowly added into the solution of berberine hydrochloride, and sufficiently stirred for full reaction, the temperature thereof is lowered to yield a precipitate, the precipitate was then filtered, a resulted solid was then vacuum dried at 60° C. and ground to yield an orange yellow solid dihydrate of the mangiferin-6-O-berberine salt. A yield rate was 76.2%, and a sample purity was 99.5% through a high performance liquid chromatography (HPLC) measurement

Preparation Example 4: Preparation of the mangiferin-6-O-berberine salt 0.05 mol of the mangiferin-6-O-calcium salt prepared in the above examples was weighed and added into a suitable amount of 70° C. water and dissolved therein to formulate a solution having a concentration of 2% (w/v), and the solution was filtered for future use; 0.1 mol of berberine hydrochloride was weighed and added into a suitable amount of 90° C. water and dissolved therein to formulate a solution having a concentration of 1% (w/v), and the solution was filtered for future use; and the solution of the mangiferin-6-O-calcium salt was slowly added into the solution of the berberine hydrochloride, and sufficiently stirred for full reaction, the temperature thereof is lowered to yield a precipitate, the precipitate was then filtered and washed with purified water sufficiently, a resulted solid was then vacuum dried at 50° C. and ground to yield an orange yellow solid mangiferin-6-O-berberine salt. A yield rate was 76.2%, and a sample purity was 99.6% through a high performance liquid chromatography (HPLC) measurement

Preparation Example 5: Preparation of the mangiferin-6-O-berberine salt 0.05 mol of the mangiferin-6-O-calcium salt prepared in the above examples was weighed and added into a suitable amount of 90° C. water and dissolved therein to formulate a solution having a concentration of 1.5% (w/v), and the solution was filtered for future use; 0.05 mol of berberine hydrochloride and 0.05 mol of berberine sulfate were weighed and added into a suitable amount of 80° C. water and dissolved therein to formulate a solution having a concentration of 1.5% (w/v), and the solution was filtered for future use; and the solution of the mangiferin-6-O-calcium salt was slowly added into the solution of the berberine hydrochloride, and sufficiently stirred for full reaction to yield a precipitate, the precipitate was then filtered and washed with purified water sufficiently, a resulted solid was then vacuum dried at 55° C. and ground to yield an orange yellow solid mangiferin-6-O-berberine salt. A yield rate was 78.2%, and a sample purity was 99.6% through a high performance liquid chromatography (HPLC) measurement The above specific examples are used for further illustrating the present invention instead of limiting the present invention.

INDUSTRIAL PRACTICABILITY

The compound preparation process according to the present invention reduces the environmental protection pressure caused by use of a large amount of organic solvents, and lowers the cost in the preparation of the mangiferin-6-O-berberine salt, and is thus more suitable for industrial production.

What is claimed is:
1. A mangiferin-6-O-calcium salt, wherein the mangiferin-6-O-calcium salt has a structure as defined in the following formula (I):

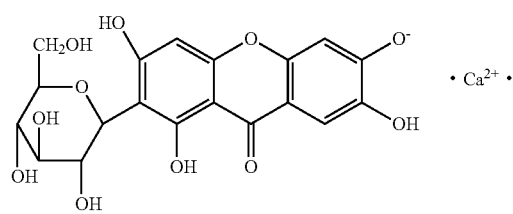 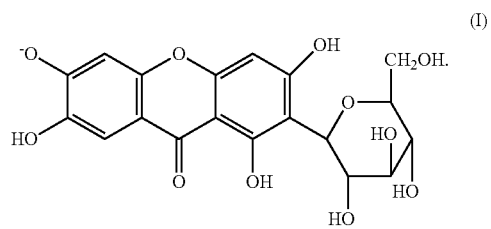

(I)

wherein a spectrum data of the mangiferin-6-O-calcium salt is as follows:

$^{13}$CNMR (400 MHz, DMSO-$d_6$) (δppm): 161.62 (C-1), 106.97 (C-2), 163.62 (C-3), 93.25 (C-4), 155.98 (C-4a), 100.53 (C-4b), 100.89 (C-5), 164.74 (C-6), 147.10 (C-7), 103.27 (C-8), 106.22 (C-8a), 153.52 (C-8b), 177.79 (C-9), 73.51 (C-1'), 70.34 (C-2'), 79.14 (C-3'), 70.34 (C-4'), 81.37 (C-5'), 60.27 (C-6').

2. A preparation process of the mangiferin-6-O-calcium salt as defined in claim 1, wherein the preparation process comprises:
(1) adding an alkaline sodium salt or an alkaline potassium salt into water to yield a solution of the alkaline sodium salt or a solution of the alkaline potassiumn salt, the solution having a concentration of 0.1%-2% (w/v);
(2) dissolving mangiferin into dimethyl sulfoxide to yield a solution of the mangiferin;

5. The preparation process according to claim 2, wherein a molar ratio of the mangiferin to the water-soluble calcium salt is 1:0.5-1.

6. The preparation process of the mangiferin-6-O-calcium salt according to claim 2, wherein the alkaline sodium salt or alkaline potassium salt is one or a mixture of more than two selected from the group consisting of sodium carbonate, sodium hydrogen carbonate, potassium carbonate and potassium hydrogen carbonate; and the water-soluble calcium salt is one or a mixture of more than two selected from the group consisting of calcium chloride, calcium gluconate, calcium lactate and calcium levulinate.

7. A preparation method of a mangiferin-6-O-berberine salt by using the mangiferin-6-O-calcium salt as claimed in claim 1, and the mangiferin-6-O-berberine salt has a structure of:

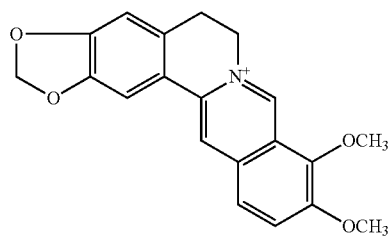 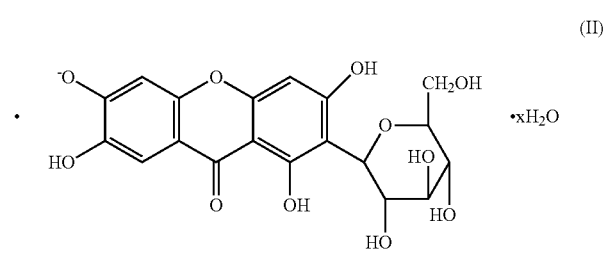

(II)

(3) slowly adding the mangiferin solution into the solution of the alkaline sodium salt or the solution of the alkaline potassium salt, fully stirring the solution until the solution is fully reacted at a temperature of 50° C.-100° C. to yield a solution of a mangiferin sodium salt or a solution of a mangiferin potassium salt;
(4) dissolving a water-soluble calcium salt into water to yield a solution of the calcium salt;
(5) sufficiently mixing the solution of the calcium salt with the solution of the mangiferin sodium salt or the solution of the mangiferin potassium salt for full reaction, yielding a precipitate, and filtering to yield a solid; and dissolving the solid into a suitable amount of hot water, filtering and yielding a precipitate, and filtering the precipitate to obtain a solid;
(6) drying the solid to yield the mangiferin-6-O-calcium salt.

3. The preparation process according to claim 2, wherein a ratio of the mangiferin to the dimethyl sulfoxide is 1:0.2-5 (w/v).

4. The preparation process according to claim 2, wherein a molar ratio of the mangiferin to the alkaline sodium salt or the alkaline potassium salt is 1:0.5-1.

wherein 0≤x≤4.

8. The method according to claim 7, wherein x=1, 2, 3, or 4.

9. The method according to claim 7, wherein the preparation method of the mangiferin-6-O-berberine salt with the mangiferin-6-O-calcium salt as the intermediate comprises:
(1) dissolving the mangiferin-6-O-calcium salt into 50-100° C. water to yield a solution of the mangiferin-6-O-calcium salt;
(2) dissolving berberine hydrochloride into 50-100° C. water to yield a solution of the berberine hydrochloride;
(3) sufficiently mixing the solution of the berberine hydrochloride with the solution of the mangiferin-6-O-calcium salt for full reaction to yield a precipitate, and filtering and washing the precipitate to yield a solid; and
(6) drying the solid to yield the mangiferin-6-O-berberine salt.

10. The method according to claim 9, wherein the solution of the mangiferin-6-O-calcium salt has a concentration of 0.1%-3%.

11. The method according to claim 9, wherein the solution of the mangiferin-6-O-calcium salt has a concentration of 1%-2%.

12. The method according to claim 9, wherein the solution of the berberine hydrochloride has a concentration of 0.1%-4%.

13. The method according to claim 9, wherein the solution of the berberine hydrochloride has a concentration of 1%-2%.

14. The method according to claim 9, wherein the in preparation of the mangiferin-6-O-berberine salt with the mangiferin-6-O-calcium salt as the intermediate, a molar ratio of the mangiferin-6-O-calcium salt to the berberine hydrochloride is 0.5:1.

15. The method according to claim 9, wherein the berberine hydrochloride is substitutable by a berberine sulfate or another medically acceptable salt of berberine.

* * * * *